United States Patent
Kang et al.

(10) Patent No.: US 12,390,350 B2
(45) Date of Patent: Aug. 19, 2025

(54) FEMUR SIZE MEASURING DEVICE

(71) Applicants: SKYVE Co., Ltd., Seoul (KR);
Kyoung Tak Kang, Seoul (KR);
Hyoung Taek Hong, Incheon (KR)

(72) Inventors: Kyoung Tak Kang, Seoul (KR);
Hyoung Taek Hong, Incheon (KR);
Yong Gon Koh, Seoul (KR)

(73) Assignees: SKYVE CO., LTD., Seoul (KR);
Kyoung Tak Kang, Seoul (KR);
Hyoung Taek Hong, Incheon (KR)

( * ) Notice: Subject to any disclaimer, the term of this patent is extended or adjusted under 35 U.S.C. 154(b) by 198 days.

(21) Appl. No.: 18/458,340

(22) Filed: Aug. 30, 2023

(65) Prior Publication Data

US 2024/0415672 A1 Dec. 19, 2024

(30) Foreign Application Priority Data

Jun. 16, 2023 (KR) .................. 10-2023-0077308

(51) Int. Cl.
*A61F 2/46* (2006.01)
*A61F 2/38* (2006.01)

(52) U.S. Cl.
CPC ............ *A61F 2/461* (2013.01); *A61F 2/3859* (2013.01); *A61F 2002/4658* (2013.01)

(58) Field of Classification Search
CPC . A61B 17/154; A61B 17/155; A61B 17/1764; A61F 2/4657; A61F 2002/4658; A61F 2090/061

See application file for complete search history.

(56) References Cited

U.S. PATENT DOCUMENTS

| | | | | |
|---|---|---|---|---|
| 5,423,827 A * | 6/1995 | Mumme | ............ | A61B 17/1764 408/115 R |
| 5,662,656 A * | 9/1997 | White | ................. | A61B 17/155 606/88 |
| 6,013,081 A * | 1/2000 | Burkinshaw | ......... | A61B 17/155 606/88 |
| 6,458,135 B1 * | 10/2002 | Harwin | ................ | A61B 17/155 606/88 |
| 7,451,550 B2 * | 11/2008 | Dees, Jr. | ............... | A61F 2/4657 606/88 |

(Continued)

FOREIGN PATENT DOCUMENTS

KR 10-2016-0119823 A 10/2016

*Primary Examiner* — Matthew J Lawson
(74) *Attorney, Agent, or Firm* — You & IP, LLC

(57) ABSTRACT

A femur size measuring device include a stylus part including a stylus arm and a stylus holder, an anterior posterior (AP) sizer part having the stylus part coupled to an upper end, a pair of paddles at a lower portion, and an anterior pin guide mount and a posterior pin guide mount, a plurality of anterior pin guides mounted to be replaceable in the anterior pin guide mount, configured to determine insertion positions of a pair of anterior position determination pins for determining a rotation position of a femur cutting guide, and configured to guide the anterior position determination pins, and a plurality of posterior pin guides mounted to be replaceable in the posterior pin guide mount, configured to determine insertion positions of a pair of posterior position determination pins for determining a rotation position of a femur cutting guide, and configured to guide the posterior position determination pins.

20 Claims, 10 Drawing Sheets

(56) References Cited

U.S. PATENT DOCUMENTS

| | | | |
|---|---|---|---|
| 7,488,324 B1* | 2/2009 | Metzger | A61F 2/4657 |
| | | | 600/587 |
| 8,216,244 B2* | 7/2012 | Green | A61B 17/1764 |
| | | | 606/88 |
| 9,113,913 B2* | 8/2015 | Reeve | A61B 17/15 |
| 9,216,026 B2 | 12/2015 | Reeve et al. | |
| 9,848,896 B2* | 12/2017 | Emslie | A61B 17/1764 |
| 10,751,199 B2 | 8/2020 | Rosen et al. | |
| 10,874,527 B2* | 12/2020 | Fulton | A61B 17/1764 |
| 2004/0220583 A1* | 11/2004 | Pieczynski, II | A61B 17/1764 |
| | | | 606/102 |
| 2007/0173851 A1* | 7/2007 | McMillen | A61B 90/06 |
| | | | 606/87 |
| 2008/0161824 A1* | 7/2008 | McMillen | A61B 17/155 |
| | | | 606/88 |
| 2014/0025081 A1* | 1/2014 | Lorio | A61B 17/025 |
| | | | 606/102 |
| 2015/0209158 A1* | 7/2015 | Reeve | A61F 2/4684 |
| | | | 606/88 |
| 2016/0089167 A1* | 3/2016 | Lin | A61B 17/155 |
| | | | 606/88 |
| 2016/0361178 A1* | 12/2016 | Budhabhatti | A61B 17/1764 |
| 2017/0079739 A1* | 3/2017 | Logan | A61B 90/06 |
| 2024/0024130 A1* | 1/2024 | Vouaux | A61F 2/4657 |

\* cited by examiner

FEMUR SIZE MEASURING DEVICE

CROSS REFERENCE TO RELATED APPLICATION

The present application claims priority to Korean Patent Applications No. 10-2023-0077308, filed Jun. 16, 2023, the entire contents of which are incorporated herein for all purposes by this reference.

BACKGROUND

Technical Field

The present disclosure relates to a femur size measuring device and, particularly, a femur size measuring device that is used to measure the actual size of a distal femur to determine the size of a femur-side prosthesis in total knee replacement.

Description of the Related Art

A knee joint means a joint composed of three adjacent bones of a femur (also called a 'thighbone'), a tibia (also called a 'shinbone'), and a patella (also called a 'kneecap') that surround a knee. A knee joint exists at both of left and right legs and corresponds to the most important joint that enables bipedalism of a human body in cooperation with coxae.

A knee joint has a high possibility of injury due to high frequency of use for the characteristics. The function of a knee joint may be deteriorated or lost particularly due to the reasons such as friction or aging of bone tissues, and bones, ligaments, etc. are injured by gradual injury or degenerative variation of cartilages due to such deterioration or loss, which may cause inflammation and pain. This is called degenerative arthritis.

In general, lifestyle improvement or conservative treatments such as medication and physical therapy are generally used to treat degenerative arthritis. However, such treatment methods only reduce the progress speed of degenerative arthritis or temporarily attenuate pain and are not fundamental solutions. In particular, it is difficult to handle degenerative arthritis through medication or physical therapy due to extreme aggravation in some cases.

Total knee replacement is a treatment that is applied to patients who still have pain and have difficulty in walking even though they receive medication or physical therapy due to extreme aggravation of degenerative arthritis. Total knee replacement is a surgical operation of cutting off a joint surface of a severely worn joint and then replacing the cutoff portion with an artificial knee joint, and artificial knee joints that are used in this case are generally composed of a femur component, a tibia component, and a bearing component.

A femur component is implanted at the place where the joint surface of a severely worn femur joint (hereafter, referred to as 'femur distal surface') has been cut and a tibia component is implanted at the place where the joint surface of at the upper end of a tibia adjacent to the femur joint has been cut. Further, a bearing component is positioned between the femur component and the tibia component and functions as a kind of cartilage to that the joint surfaces can be smoothly moved well.

When implanting a femur component on a femur distal surface, it is important to select an appropriate femur component fitting the bone on which the femur component is implanted. Since people have femurs of different sizes, it is required to select appropriate femur components fitting the femurs of patients, and as pre-work for such selection, the size of a distal femur is measured using a femur size measuring device.

A femur size measuring device is an instrument that is used to measure the size of an actual distal femur (the joint part of a femur far from the body) and determine a femur component with an appropriate size in correspondence to the measured size. Various configurations including U.S. Pat. Nos. 10,751,199 and 9,216,026 have been known as femur size measuring devices according to the related art.

In order to measure the size of a distal femur using a femur size measuring device, a distal surface of a femur is horizontally cut off, the femur size measuring device is attached to the resected surface, and then the size of the femur is measured. An instrument such as a distal femur cutting block may be used to form a resected surface that is obtained by horizontally cutting off the distal surface of a femur.

A femur component may be provided in standard dimensions of various sizes. When a femur component that fits a femur of a patient is determined by measuring the femur size, it is required to determine an accurate implantation position of the femur component with respect to the distal femur. Since a femur component fitting to the size of bones of a patient is selected, it may be considered as an important factor to determine the position of a femur component with respect to a femur when implementing the inherent natural knee joint motion of the patient.

When the size of a distal femur is measured using a femur size measuring device, a pin for determining the position of a femur component is inserted in the femur. Further, a femur cutting guide is fixed at a target position on the femur using the inserted pin, and anterior cutting, posterior cutting, anterior chamfer cutting, and posterior chamfer cutting are performed, whereby the distal femur is machined into a shape suitable for attaching the femur component.

The position of a femur component with respect to a distal femur can be determined generally through two kinds of surgical approaches. One of the approaches is to put a referencing point for determining the position of a femur cutting guide at the anterior part of a distal femur and the other one is to put the referencing point at a posterior condyle of a distal femur.

The anterior referencing method that puts a referencing point at the anterior part of a distal femur has the advantage that it is advantageous in notch control of a resected cross-section of the distal femur. A posterior referencing method has the advantage that the resection depth toward the posterior part of a distal femur is constant, approach is easier than the anterior referencing, and the operating time can be reduced.

The anterior referencing method puts a referencing point at the anterior part of a distal femur, so it is possible to relatively accurately determine the position of a femur cutting guide with respect to the anterior part of the distal femur, and the posterior referencing method puts a referencing point at the posterior part of a distal femur, so it is possible to relatively accurately determine the position of a femur cutting guide with respect to the posterior part of the distal femur.

Such referencing methods that are used to determine the fixing point of a femur cutting guide when measuring a femur size of a patient using a femur size measuring device have their own advantages. Accordingly, in the related art, surgical operations are performed in the way of selecting an appropriate method from the two methods in consideration of the shape of a femur, the difficulty of a corresponding surgical operation, or the like and then appropriately determining the fixing position of a femur cutting guide.

However, since two kinds of femur size measuring devices designed to be suitable for corresponding methods are required in order to determine the fixing position of a femur cutting guide through the anterior referencing method or determine the fixing position of a femur cutting guide using the posterior referencing method, so there is a problem that the economic load is unavoidably large.

Prior Art Document (Patent Document 1) U.S. Pat. No. 10,751,199 (registration date: 2020 Aug. 25.)
(Patent Document 2) U.S. Pat. No. 9,216,026 (registration No. 2015Dec. 22.)

SUMMARY

An objective of the present disclosure is to provide a femur size measuring device that can perform not only femur size measurement, but an appropriate surgical approach (anterior referencing or posterior referencing) considering the shape of a femur of a patient and the difficulty of the corresponding surgical operation through one device.

Another objective of the present disclosure is to provide a femur size measuring device that can determine an appropriate implantation position or direction of a femur component (femur prosthesis) to implement the inherent natural knee joint motion of a patient in the process of measuring the size of a femur.

In order to achieve the objectives, according to an embodiment of the present disclosure, there is provided a femur size measuring device that is a device used to measure the size of a distal femur to determine the size of a femur-side prosthesis (femur component) in total knee replacement, and includes: a stylus part including a stylus arm and a stylus holder to which the stylus arm is coupled to be able to move forward and backward; an anterior posterior (AP) sizer part having the stylus part coupled to an upper end thereof, having a pair of paddles at a lower portion thereof, and having an anterior pin guide mount and a posterior pin guide mount; a plurality of anterior pin guides mounted to be replaceable in the anterior pin guide mount, configured to determine insertion positions of a pair of anterior position determination pins for determining a rotation position of a femur cutting guide to be attached to a distal resected surface in a following process after a size of a distal femur is measured, and configured to guide the anterior position determination pins such that the anterior position determination pins can be accurately inserted at the determined insertion positions; and a plurality of posterior pin guides mounted to be replaceable in the posterior pin guide mount, configured to determine insertion positions of a pair of posterior position determination pins for determining a rotation position of a femur cutting guide to be attached to a distal resected surface in a following process after a size of a distal femur is measured, and configured to guide the posterior position determination pins such that the posterior position determination pins can be accurately inserted at the determined insertion positions.

In the femur size measuring device according to an embodiment of the present disclosure, the AP sizer part may include: an upper AP sizer having the stylus part coupled thereto and having a seat with an open bottom; a lower AP sizer having the pair of paddles and a connection member that is coupled to the seat to be slidable up and down and has size indication marks inscribed on a surface thereof; and a locking member installed through portions of both of the upper AP sizer and the lower AP sizer to allow or restrict sliding of the connection member relative to the seat, and the anterior pin guide mount may be formed at the upper AP sizer and the posterior pin guide mount may be formed at the lower AP sizer.

In this case, a fastening protrusion composed of an anterior fastening section and a posterior fastening section may be formed in a predetermined height at a center of the seat, a fastening groove having an oblong hole may be formed at the connection member in correspondence to the fastening protrusion, and a portion of the locking member may be thread-fastened to a posterior through-hole of the posterior fastening section through both an anterior through-hole of the anterior fastening section and the oblong hole.

The anterior pin guide mount formed at the AP sizer part, preferably, may have: a first anterior pin guide mount hole formed at a first side of the upper AP sizer constituting the AP sizer part; and a second anterior pin guide mount hole formed at a second side of the upper AP sizer to be symmetric to the first anterior pin guide mount hole, and the posterior pin guide mount may have: a first posterior pin guide mount hole formed at a first side of a body of the lower AP sizer constituting the AP sizer part; and a second posterior pin guide mount hole formed at a second side of the body to be symmetric to the first posterior pin guide mount hole.

Further, a paddle block may be integrally formed under the body of the lower AP sizer, and the pair of paddles provided such that the condylus medialis and the condylus lateralis of a posterior part of a distal femur come in contact with the pair of paddles, respectively, when a size of the distal femur is measured may be connected to the paddle block.

Preferably, a pair of fixing pin insertion holes in which fixing pins configured to fix the AP sizer part to a distal resected surface of a distal femur may be formed at the body of the lower AP sizer.

Further, the anterior pin guides applied to an embodiment of the present disclosure each may include: a first anterior guide inserted in a first anterior pin guide mount hole or a second anterior pin guide mount hole of the anterior pin guide mount, and having an anterior reference position determination hole; a second anterior guide inserted in the second anterior pin guide mount hole or the first anterior pin guide mount hole, and having an anterior rotation position determination hole in correspondence to the anterior reference position determination hole; a connection bridge connecting the first anterior guide and the second anterior guide to each other.

As a preferred embodiment, one anterior reference position determination hole and one anterior rotation position determination hole may be formed, respectively, at the first anterior guide and the second anterior guide of each of the anterior pin guides.

In this case, a center point of the anterior reference position determination hole and a center point of the anterior rotation position determination hole of one of the plurality of anterior pin guides may be arranged horizontally at the same height, and a center point of the anterior reference position determination hole and a center point of the corresponding anterior rotation position determination hole of the others may be arranged at different heights.

As another preferred embodiment, two anterior reference position determination holes and two anterior rotation position determination holes may be formed, respectively, at the first anterior guide and the second anterior guide of each of the anterior pin guides.

In this case, one of the plurality of anterior pin guides may include an anterior reference position determination hole and an anterior rotation position determination hole of which center points are arranged horizontally at the same height, and a center point of the anterior reference position determination hole and a center point of the corresponding anterior rotation position determination hole of the others may be arranged horizontally at different heights.

Preferably, an angle indication mark showing the degree of inclination of a virtual straight line, which connects the center points of the anterior reference position determination hole and the anterior rotation position determination hole that correspond to each other, relative to a horizontal reference line may be inscribed around the anterior reference position determination hole and the corresponding anterior rotation position determination hole; and Considering the anatomical shape of the anterior part of a distal femur, a horizontal distance from a center of the anterior reference position determination hole and a center point of the anterior rotation position determination hole may be 25 mm~40 mm.

Further, the posterior pin guides applied to an embodiment of the present disclosure each may include: a first posterior guide inserted in a first posterior pin guide mount hole or a second posterior pin guide mount hole of the posterior pin guide mount, and having a posterior reference position determination hole; a second posterior guide inserted in the second posterior pin guide mount hole or the first posterior pin guide mount hole, and having a posterior rotation position determination hole in correspondence to the posterior reference position determination hole; and a connection bridge connecting the first posterior guide and the second posterior guide to each other.

In this case, one posterior reference position determination hole and one posterior rotation position determination hole may be formed, respectively, at the first posterior guide and the second posterior guide of each of the posterior pin guides.

In this case, a center point of the posterior reference position determination hole and a center point of the posterior rotation position determination hole of one of the plurality of posterior pin guides may be arranged horizontally at the same height, and a center point of the posterior reference position determination hole and a center point of the corresponding posterior rotation position determination hole of the others may be arranged at different heights.

Two posterior reference position determination holes and two posterior rotation position determination holes may also be formed, respectively, at the first posterior guide and the second posterior guide of each of the posterior pin guides.

In this case, one of the plurality of posterior pin guides includes a posterior reference position determination hole and a posterior rotation position determination hole of which center points may be arranged horizontally at the same height, and a center point of the posterior reference position determination hole and a center point of the corresponding posterior rotation position determination hole of the others may be arranged horizontally at different heights.

Preferably, an angle indication mark showing the degree of inclination of a virtual straight line, which connects the center points of the posterior reference position determination hole and the posterior rotation position determination hole that correspond to each other, relative to a horizontal reference line is inscribed also around the posterior reference position determination hole and the corresponding posterior rotation position determination hole; and Considering the anatomical shape of the posterior part of a distal femur, a horizontal distance from a center of the posterior reference position determination hole and a center point of the posterior rotation position determination hole may be 35 mm~50 mm.

According to an embodiment of the present disclosure, if necessary, it is possible to mount and use an anterior pine guide in an anterior pin guide mount (in the case of anterior referencing) or mount and use a posterior pin guide in a posterior pin guide mount (in the case of posterior referencing). That is, it is possible to perform appropriate surgical approach considering the shape of a femur of a patient or the difficulty of a corresponding surgical operation through one device even without using two kinds of femur size measuring device like in the related art.

Further, since pluralities of anterior pin guides and posterior pin guides are provided and pairs of position determination holes for determining the rotation position of a femur cutting guide are formed at different angles at the pin guides, it is possible to determine an appropriate implantation position or direction of a femur component (femur prosthesis) in the process of measuring the size of a distal femur when implementing the inherent natural knee joint motion of a patient.

BRIEF DESCRIPTION OF THE DRAWINGS

The above and other objectives, features and other advantages of the present disclosure will be more clearly understood from the following detailed description when taken in conjunction with the accompanying drawings, in which.

DETAILED DESCRIPTION

Figure 1:
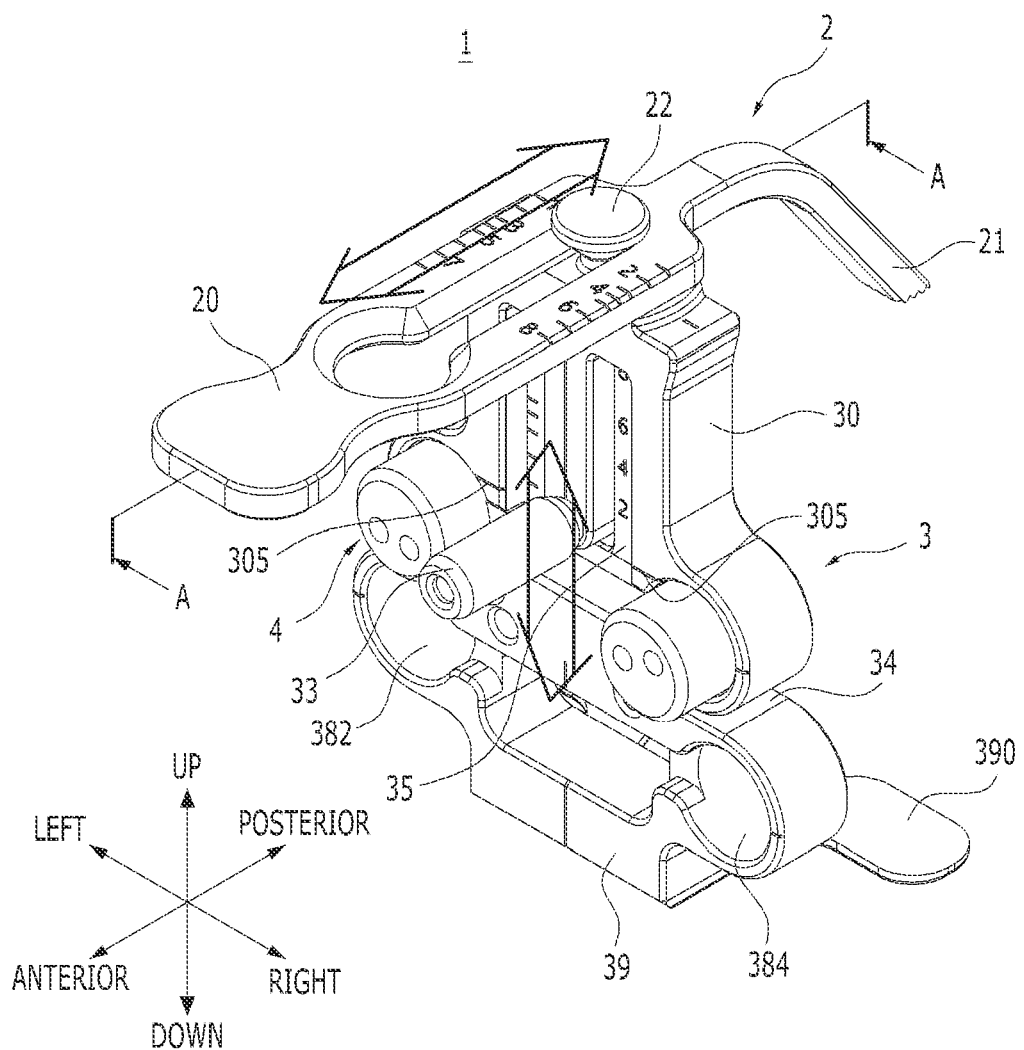
FIG. 1 is a perspective view of a femur size measuring device according to an embodiment of the present disclosure.

Hereinafter, exemplary embodiments of the present disclosure are described in detail with reference to the accompanying drawings.

The terminologies used herein are used just for the purpose of describing particular embodiments and are not intended to limit the present disclosure. Singular forms are intended to include plural forms unless the context clearly indicates otherwise.

It will be further understood that the terms "comprise" or "have" used in this specification, specify the presence of stated features, steps, operations, components, parts, or a combination thereof, but do not preclude the presence or addition of one or more other features, numerals, steps, operations, components, parts, or a combination thereof.

Terms used in the specification, "first", "second", etc., may be used to describe various components, but the components are not to be construed as being limited to the terms. The terms are used only to distinguish one component from another component.

In the following description referring to the accompanying drawings, the same components are given the same reference numerals and are not repeatedly described. However, in describing the present disclosure, detailed descriptions of well-known technologies will be omitted so as not to obscure the description of the present disclosure with unnecessary detail.

Figure 2:
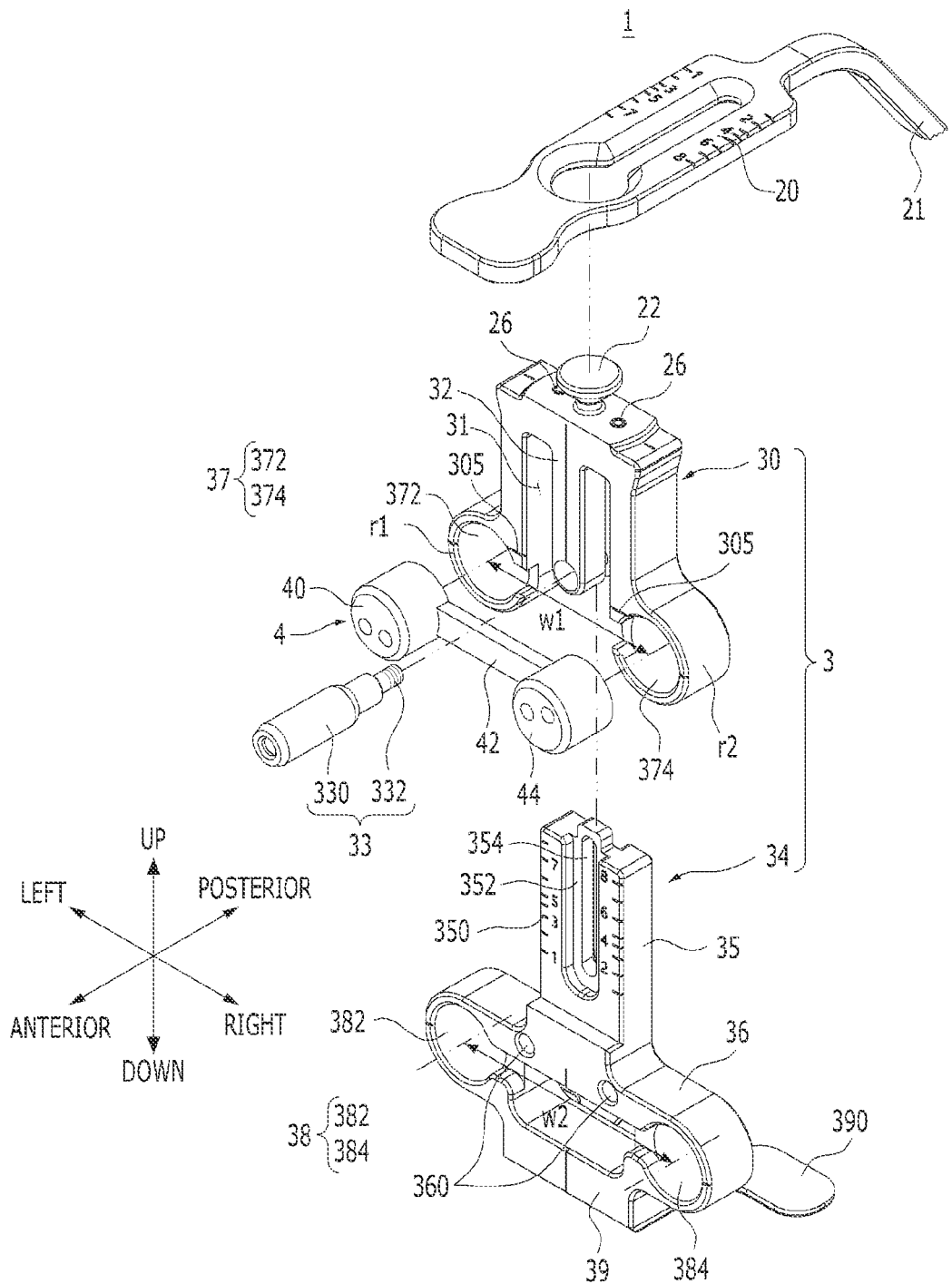
FIG. 2 is an exploded perspective view of the femur size measuring device according to an embodiment of the present disclosure shown in FIG. 1.
Figure 3:
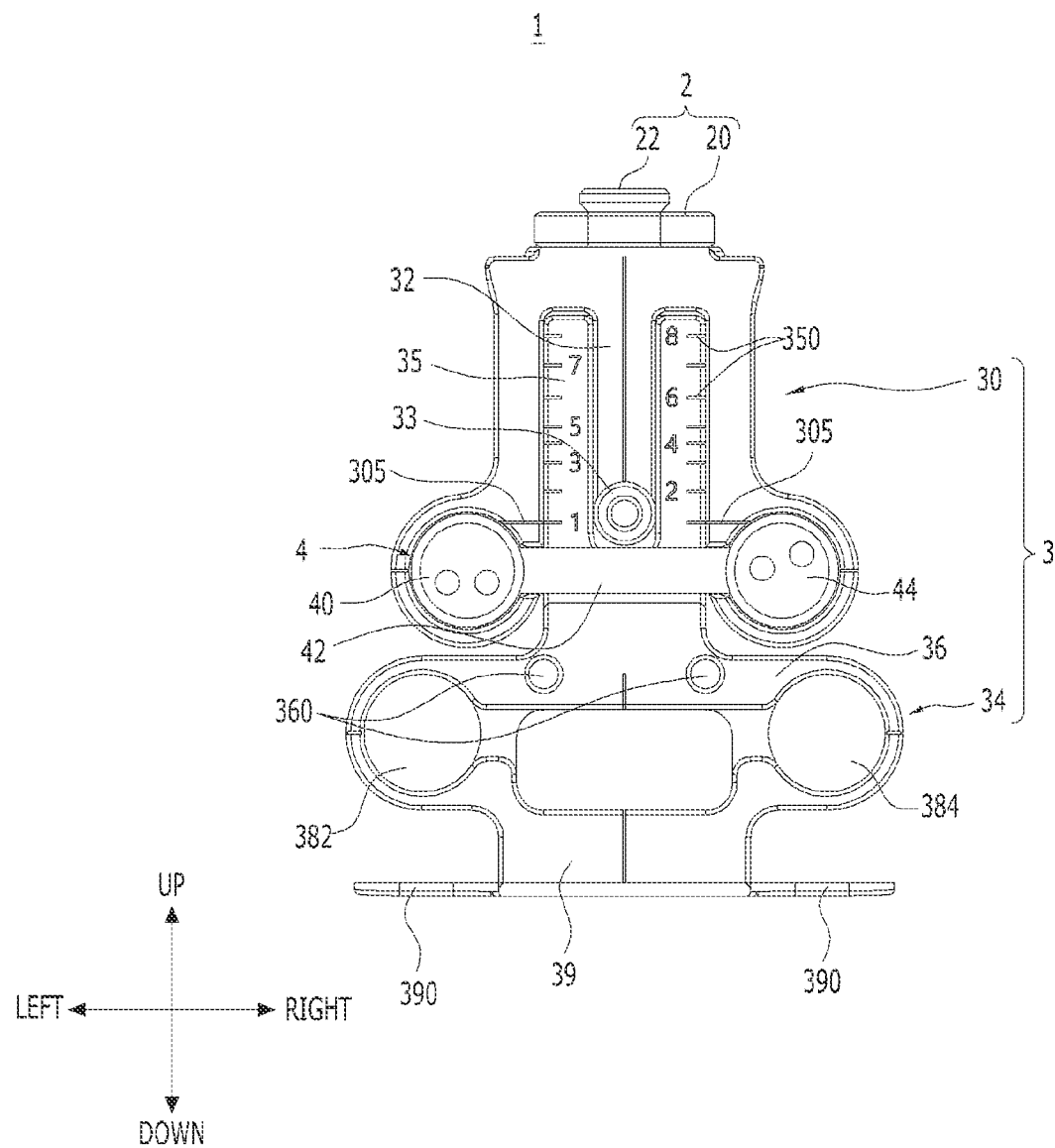
FIG. 3 is a front view of the femur size measuring device according to an embodiment of the present disclosure shown in FIG. 1.
Figure 4:
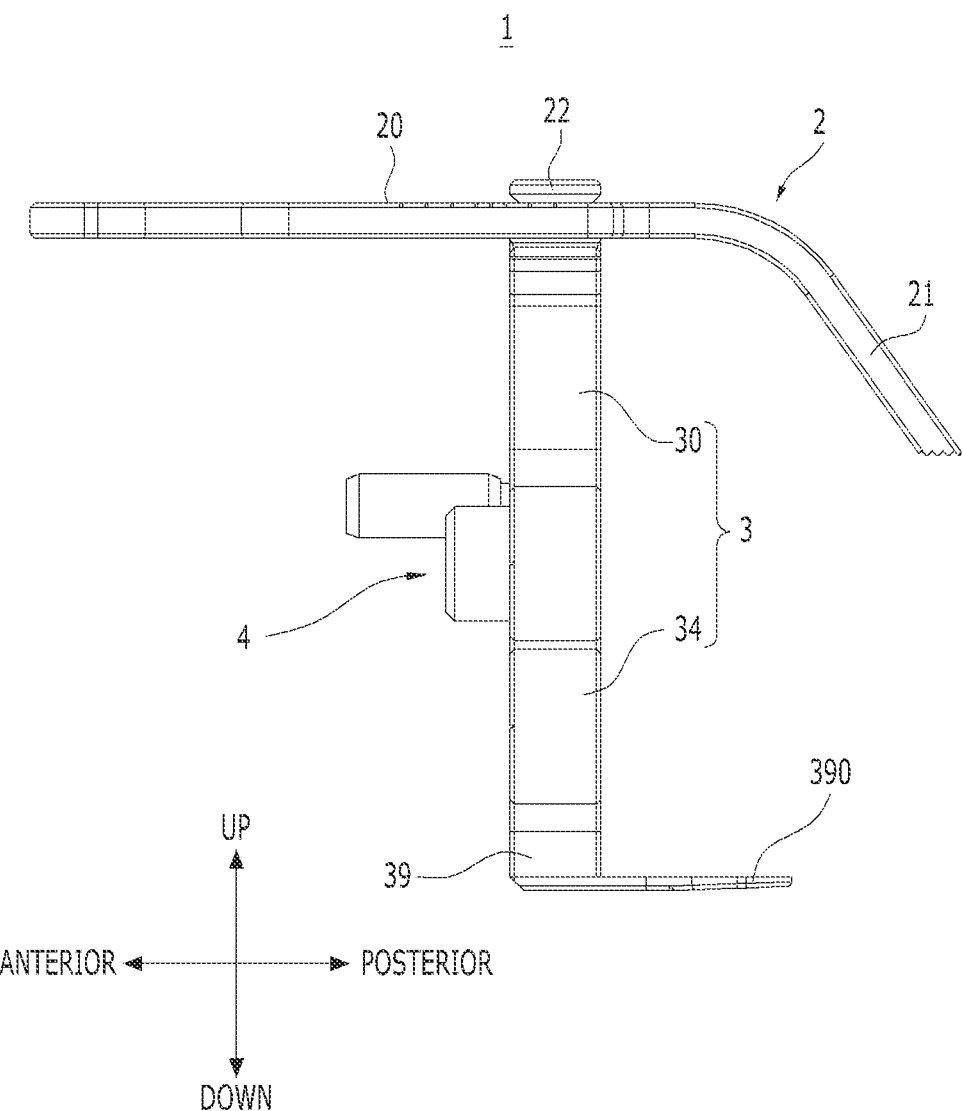
FIG. 4 is a side view of the femur size measuring device according to an embodiment of the present disclosure shown in FIG. 1.
Figure 5:
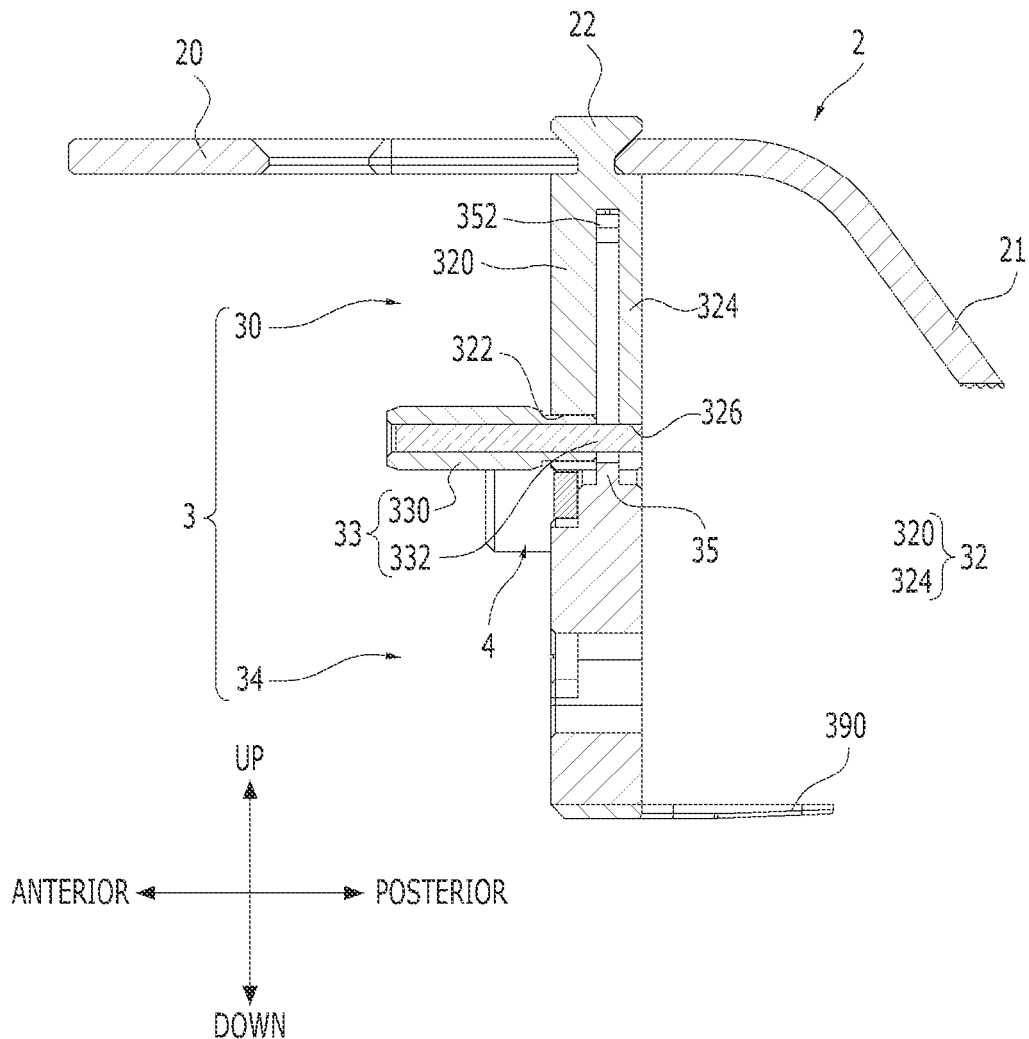
FIG. 5 is a cross-sectional view taken along line A-A of the femur size measuring device shown in FIG. 1.

FIG. 1 is a perspective view of a femur size measuring device according to an embodiment of the present disclosure and FIG. 2 is an exploded perspective view of the femur size measuring device according to an embodiment of the present disclosure shown in FIG. 1. FIGS. 3 and 4 are views showing the femur size measuring device according to an embodiment of the present disclosure shown in FIG. 1 from the front and the side, respectively and FIG. 5 is a cross-sectional view taken along line A-A of the femur size measuring device shown in FIG. 1.

Referring to FIGS. 1 to 5, a femur size measuring device according 1 to an embodiment of the present disclosure is a device that is used to measure the size of a distal femur in order to determine the size of a femur-side prosthesis (femur component) in total knee replacement, and, in a broad meaning, may be composed of a stylus part 2, an anterior posterior (AP) sizer part 3, an anterior pin guide, and a posterior pin guide.

The stylus part 2 includes a stylus arm 20. The stylus part 2 may further include a stylus holder 22 to which the stylus arm 20 is coupled to be able to move forward and backward. The stylus holder 22 may be disposed on the upper end of the AP sizer part 3 in an integrated or separated type, and the stylus arm 20 may be coupled to the stylus holder 22 to be able to move forward and backward within a predetermined range in the direction coordinate system shown in the figures.

The stylus arm 20, as exemplified in FIG. 2, may be coupled to the stylus holder 22 in the structure in which stylus arm 20 is fixed at forward and backward operates positions in close contact with the bottom of the stylus holder 22 by ball plungers 26 installed in the top of the AP sizer part 3, and a stylus tip 21 may be disposed at the front end of the stylus arm 20. The stylus tip 21 may be inclined downward at a predetermined angle, as in the example shown in the figures.

Since the stylus tip 21 is brought in contact or close contact with a predetermined position on an anterior surface of a distal femur when the size of the distal femur is measured, a doctor can see the point where a cutting blade passes through the anterior part of a distal femur when performing resection of the distal femur, in more detail, anterior chamfer cutting of the distal femur that is performed in the following process.

The AP sizer part 3 has the stylus part 2 at the upper end thereof and may include a pair of paddles 390 at the lower portion with which the surface of the posterior condyle of a distal femur is brought in contact when the size of a femur is measured. An anterior pin guide mount 37 and posterior pin guide mount 38 may be formed at the AP sizer part 3.

The AP sizer part 3 may be composed of an upper AP sizer 30 and a lower AP sizer 34. The stylus part 2 is coupled to the upper end of the upper AP sizer 30 and the pair of paddles 390 with which the condylus medialis and the condylus lateralis of the posterior part of a distal femur are brought in contact when the size of a femur is measured may be disposed at the lower AP sizer 34.

The height (the up-down length in the direction coordinate system in the figures) of the AP sizer part 3 may be changed in accordance with the size of a distal femur. To this end, the upper AP sizer 30 and the lower AP sizer 34 may be coupled to each other in the structure in which the length decreases when they are folded over each other or the length increases when they are moved away from each other. That is, the upper AP sizer 30 and the lower AP sizer 34 may be coupled to each other through sliding to be able to move relatively to each other.

In order to couple the AP sizers such that they can move relatively to each other, a seat 31 with an open bottom may be formed at the upper AP sizer 30 and a connection member 35 coupled to the seat 31 to be slidable up and down and having size indication marks 350 on the surface may be disposed at the lower AP sizer 34. Sliding of the connection member 35 with respect to the seat 31 may be allowed or restricted by a locking member 33 installed through the upper AP sizer 30 and the lower AP sizer 34.

As shown in FIGS. 2 and 5, a fastening protrusion 32 may be formed in a predetermined height at the center of the seat 31 of the upper AP sizer 30. The fastening protrusion 32, preferably, may be composed of an anterior fastening section 320 and a posterior fastening section 324. In correspondence to the fastening protrusion 32, a fastening groove 352 that is coupled to the fastening protrusion 32 to be slidable up and down in the figures may be formed at the connection member 35 of the lower AP sizer 34.

The size indication marks 350 marked on the surface of the connection member 35 may be exposed to the outside through the seat 31 at both sides of the fastening protrusion 32. A reference marker 305 may be inscribed on a surface of the upper AP sizer 30. Accordingly, it is possible to select or determine the size of a femur component (femur prosthesis) by reading a size indication mark 350 on the connection member 35, which corresponds to the reference marker 305 or is positioned in a substantially same line as the reference marker 305, when measuring a femur size.

The size indication marks 350 of the connection members 35 may be inscribed as numbers, symbols, or characters, and a slot-type oblong hole 354 may be formed at the fastening groove 352 of the connection member 35 in the up-down direction in the figures. An anterior through-hole 322 and a posterior through-hole 326 may be formed at positions or heights, which correspond to each other, at the anterior fastening section 320 and the posterior fastening section 324 of the fastening protrusion 32, respectively.

The locking member 33 may be thread-fastened to the posterior through-hole 326 of the posterior fastening section 324 through both the anterior through-hole 322 and a portion of the oblong hole 354 that are aligned when the connection member 35 is slidably coupled to the seat 31. The locking member 33, preferably, may be a rotary locking member 33 having a knob 33 positioned in front of the anterior fastening section 320 and a threaded part 332 having threads that are thread-fastened to the posterior through-hole 326 of the posterior fastening section 324 at the opposite side.

Accordingly, it is possible to make the state in which a free relative motion is possible (the up-down length of the AP sizer part 3 is adjusted) by restricting or allowing a relative motion between the upper AP sizer 30 and the lower AP sizer 34 using the locking member 33.

For example, when the locking member 33 is tightened, the anterior fastening section 320 and the posterior fastening section 324 are elastically deformed toward each other at the corresponding portions and strongly press the fastening groove therebetween, whereby a relative motion, that is, sliding between the upper AP sizer 30 and the lower AP sizer 34 can be suppressed.

That is, it is possible to appropriately increase or decrease the up-down length of the AP sizer part 3 with the locking member 33 released to fit to the size of a distal femur, and when the locking member 33 is tightened again after the length of the AP sizer part 3 is appropriately adjusted to fit to the size of the distal femur, the AP sizer part 3 can be maintained in the length-adjusted state, that is, the state in which the AP sizer part 3 is stretched or contracted to fit to the size of the distal femur.

The lower AP sizer 34 may have a body 36 integrally formed under the connection member 35 and a paddle block 39 integrally formed under the body 3, and the pair of paddles 390 that is brought in contact with the condylus medialis and the condylus lateralis of the posterior part of a distal femur, respectively, when the size of the distal femur is measured can be connected to the paddle block 39.

A pair of fixing pin insertion holes 360 may be formed at the body 36 of the lower AP sizer 34. A pair of fixing pins that fixes the AP sizer part 3 to a distal resected surface of a femur can be inserted into the fixing pin insertion holes 360, and accordingly, the following work that is performed after the size of a distal femur is measured, in more detail, the work of implanting a position determination pin for determining the position of a femur cutting guide can be clearly and stably performed.

The posterior pin guide mount 37 may be formed at the upper AP sizer 30. The anterior pin guide mount 37, preferably, may be composed of a first anterior pin guide mount hole 372 formed at a first side of the upper AP sizer 30 and a second anterior pin guide mount hole 374 formed at a second side of the upper AP sizer 30 to be symmetric to the first anterior pin guide mount hole 372.

The first anterior pin guide mount hole 372 and the second anterior pin guide mount hole 374 of the anterior pin guide mount 37, for example, as shown in the figures, may be formed respectively inside a first mount ring r1 and a second mount ring r2 by the first and second mount rings that are integrally formed at the first side and the opposite second side of the AP sizer 30, but the present disclosure is not limited thereto.

The posterior pin guide mount 38 may be formed at the lower AP sizer 34. The posterior pin guide mount 38, preferably, may be composed of a first posterior pin guide mount hole 382 formed at a first side of the body of the lower AP sizer 34 and a second posterior pin guide mount hole 384 formed at a second side of the body 36 to be symmetric to the first posterior pin guide mount hole 382.

Considering the anatomical shape of a distal femur, the width w2 of the posterior pin guide mount 38 (the horizontal distance between the center point of the first posterior pin guide mount hole and the second posterior pin guide mount hole) may be larger than the width w2 of the anterior pin guide mount (the horizontal distance between the center point of the first anterior pin guide mount hole and the second anterior pin guide mount hole).

The anterior pin guide 4 that is a main component of the femur size measuring device according to the present disclosure may be detachably mounted in the anterior pin guide mount 37. Further, the posterior pin guide 5 that is another main component of the femur size measuring device according to the present disclosure may be detachably mounted in the posterior pin guide mount 38.

A plurality of anterior pin guides may be provided to be mounted to be replaceable in the anterior pin guide mounts 37, respectively. The anterior pin guide 4 serves to determine the insertion positions of a pair of anterior position determination pins P2 (hereafter, see FIG. 9) for determining the rotation position of a femur cutting guide (not shown) to be attached to a distal resected surface in the following process after the size of a distal femur is measured, and serves to guide the anterior position determination pin P2 such that the anterior position determination pin P2 can be accurately inserted at the determined insertion positions A plurality of posterior pin guides may also be provided to be mounted to be replaceable in the anterior pin guide mount 38. The posterior pin guide 5 serves to determine the insertion positions of a pair of posterior position determination pins P3 for determining the rotation position of a femur cutting guide to be attached to a distal resected surface in the following process after the size of a distal femur is measured, and serves to guide the posterior position determination pin P3 (hereafter, see FIG. 10) to be accurately inserted at the determined insertion positions The anterior pin guide 4 can be mounted and used in the anterior pin guide mount 37 to determine the position of a femur cutting guide through posterior referencing that puts a referencing point (measurement reference point) at the posterior part of a distal femur when measuring the size of the distal femur using the femur size measuring device according to an embodiment of the present disclosure.

The posterior pin guide 5 can be mounted and used in the posterior pin guide mount 38 to determine the position of a femur cutting guide through anterior referencing that puts a referencing point at the anterior part of a distal femur when measuring the size of the distal femur using the femur size measuring device according to an embodiment of the present disclosure.

That is, the femur size measuring device 1 according to an embodiment of the present disclosure, depending on necessity or selection, can provide two options through one device such as enabling the anterior pin guide 4 to be mounted and used in the anterior pin guide mount 37 or the posterior pin guide 5 to be mounted and used in the posterior pin guide mount 38.

The anterior pin guide 4 that is mounted in the anterior pin guide mount 37 and the posterior pin guide 5 that is mounted in the posterior pin guide mount 38 each may be composed of a pair of left and right guides that guides insertion of a pair of position determination pins in the distal resected surface of a femur and a portion (hereafter, referred to as a 'connection bridge 42 or 52') connecting the pair of left and right guides.

Figure 6A:
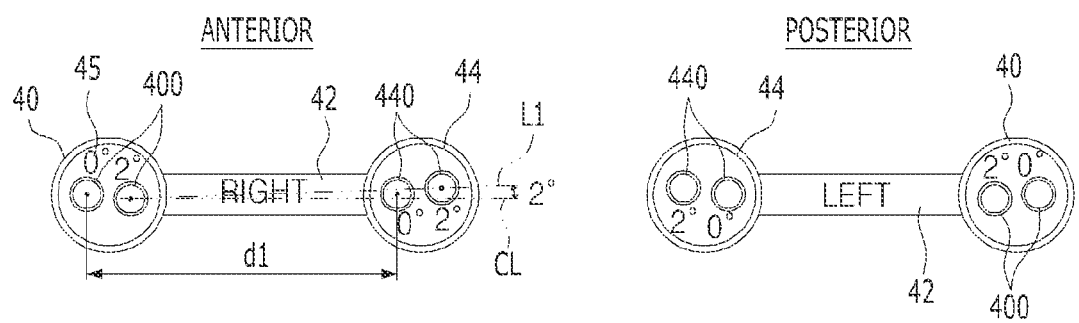
FIG. 6A, FIG. 6B, and FIG. 6C are views showing preferred embodiments of an anterior pin guide.
Figure 6B:
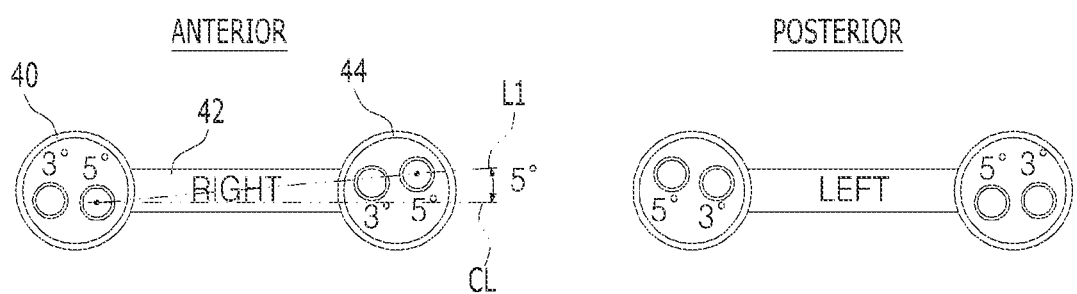
Figure 6C:
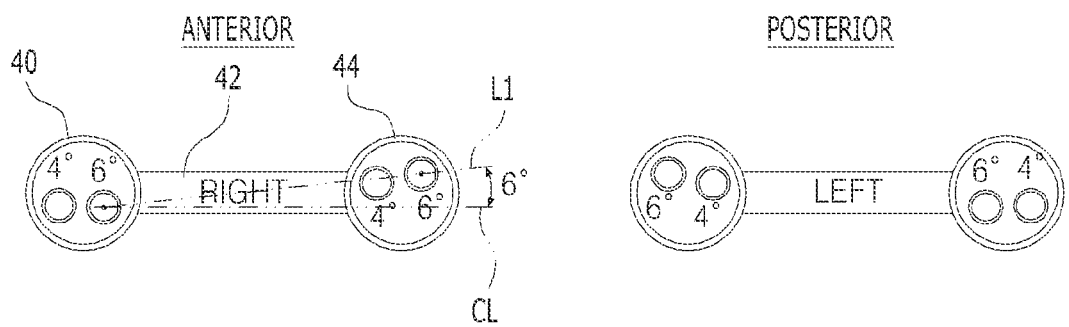
Figure 7A:
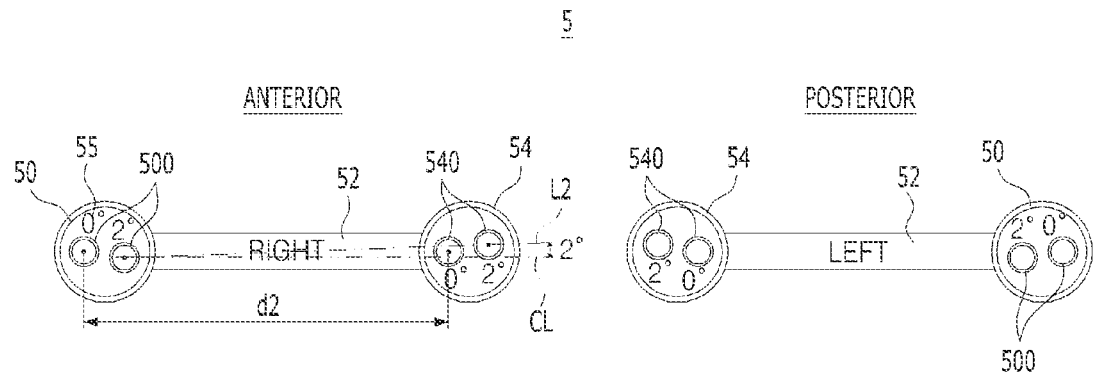
FIG. 7A, FIG. 7B, and FIG. 7C are views showing preferred embodiments of a posterior pin guide.
Figure 7B:
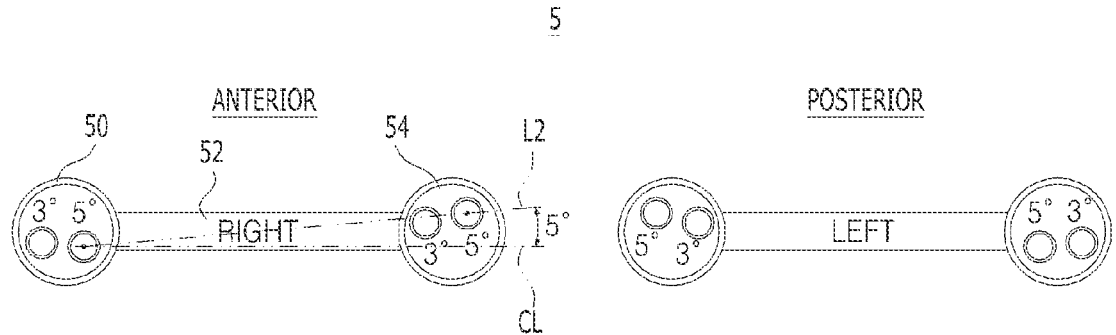
Figure 7C:
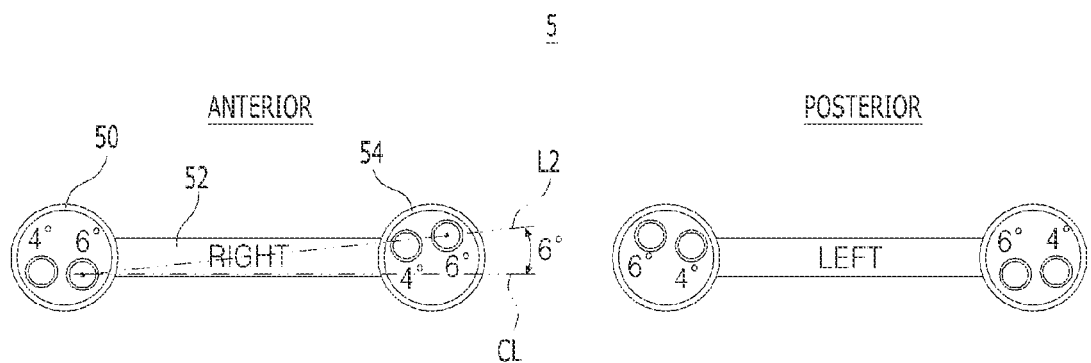

The detailed configuration of the anterior pin guide 4 and the posterior pin guide 5 is described below with reference to FIGS. 6 and 7.

FIGS. 6 and 7 are views respectively exemplifying preferred embodiments including a plurality of anterior pin guides (FIG. 6) and a plurality of posterior pin guides (FIG. 7) that are applied to the femur size measuring device according to an embodiment of the present disclosure, and the configuration in which two position determination holes are formed at each of a pair of left and right guides is exemplified.

First, referring to FIG. 6, anterior pin guides 4 each may be composed of a first anterior guide 40 having anterior reference position determination holes 400, a second anterior guide 44 having anterior in rotation position determination holes 440 correspondence to the anterior reference position determination holes 400, and a connection bridge 42 connecting the first anterior guide 40 and the second anterior guide 44.

When the femur size measuring device 1 according to an embodiment of the present disclosure is applied to a right knee joint, the first anterior guide 40 of the anterior pin guide 4 can be inserted into a first anterior pin guide mount hole 372. In this case, the second anterior guide 44 can be inserted into the second anterior pin guide mount hole 374 at the opposite side.

Alternatively, when the femur size measuring device 1 according to an embodiment of the present disclosure is applied to a left knee joint, the device 1 can be used in the way of inserting the first anterior guide 40 into the second anterior pin guide mount hole 374 and inserting the second anterior guide 44 into the first anterior pin guide mount hole 372 by turning over the anterior pin guide 4 180°

A plurality of anterior pin guides 4 may be provided. For example, as exemplified in FIG. 6, three anterior pin guides may be provided. Two anterior reference position determination holes 400 may be formed at the first anterior guide 40 of each of the anterior pin guide 4 and two rotation position determination holes 440 may be formed at the second anterior guide 44 of each of the anterior pin guides 4 in correspondence to the two anterior reference position determination holes 400.

In one of the plurality of anterior pin guides 4 (FIG. 6A), the center points of one pair of the two pairs of anterior reference position determination holes 400 and anterior rotation position determination holes 440 included in the corresponding anterior pin guide 4 may be arranged horizontally at the same height (the center points of one anterior reference position determination hole and the anterior rotation position determination hole corresponding thereto may be positioned horizontally in the same line), and the center point of the anterior reference position determination hole 400 and the center point of the anterior rotation position determination hole 440 corresponding thereto of the other pair may be arranged horizontally at different heights, that is, may be arranged horizontally in different lines.

In the other anterior pin guides (FIG. 6B and FIG. 6C) excluding the anterior pin guide (FIG. 6A), the center points of the anterior reference position determination holes 400 and the center points of the anterior rotation position determination holes 440 corresponding thereto included in each of the anterior pin guides 4 may be arranged horizontally at different heights, that is, may be arranged horizontally in different lines.

Preferably, angle indication marks 45 that show the degree of inclination of virtual straight lines L1, which connect the center points of the anterior reference position determination holes 400 and the anterior rotation position determination holes 440 that correspond to each other, relative to a horizontal reference line CL may be inscribed around the anterior reference position determination holes 400 and the anterior rotation position determination holes 440 corresponding thereto at each of the anterior pin guides 4.

The angle indication marks 45, for example, may be combinations of a number and a symbol (angle symbol), as exemplified in the figures, and the horizontal distance d1 from the center point of the anterior reference position determination hole 400 to the center point of the anterior rotation position determination hole 440 corresponding thereto may be 25 mm~40 mm when considering the anatomical shape of the anterior part of a distal femur.

Next, referring to FIG. 7, posterior pin guides 5 each may be composed of a first posterior guide 50 having a posterior reference position determination hole 500, a second posterior guide 54 having a posterior rotation position determination hole 540 in correspondence to the posterior reference position determination hole 500, and a connection bridge 52 connecting the first posterior guide 50 and the second posterior guide 54.

When the femur size measuring device 1 according to an embodiment of the present disclosure is applied to a right knee joint, the first posterior guide 50 of the posterior pin guide 5 can be inserted into a first posterior pin guide mount hole 382. In this case, the second posterior guide 54 can be inserted into the second posterior pin guide mount hole 384 at the opposite side.

Alternatively, when the femur size measuring device 1 according to an embodiment of the present disclosure is applied to a left knee joint, the device 1 can be used in the way of inserting the first posterior guide 50 into the second posterior pin guide mount hole 384 and inserting the second posterior guide 54 into the first posterior pin guide mount hole 382 by turning over the posterior pin guide 5 180°

A plurality of posterior pin guides 5 may be provided. For example, as exemplified in FIG. 7, three posterior pin guides may be provided. Two posterior reference position determination holes 500 may be formed at the first posterior guide 50 of each of the posterior pin guide 5 and two posterior rotation position determination holes 540 may be formed at the second posterior guide 54 of each of the posterior pin guides 5 in correspondence to the two posterior reference position determination holes 500.

In one of the plurality of posterior pin guides 5 (FIG. 7A), the center points of one pair of the two pairs of posterior reference position determination holes 500 and posterior rotation position determination holes 540 included in the corresponding posterior pin guide 5 may be arranged horizontally at the same height (the center points of one posterior reference position determination hole and the posterior rotation position determination hole corresponding thereto may be positioned horizontally in the same line), and the center point of the posterior reference position determination hole 500 and the center point of the posterior rotation position determination hole 540 corresponding thereto of the other pair may be arranged horizontally at different heights, that is, may be arranged horizontally in different lines.

In the other posterior pin guides (FIG. 7B and FIG. 7C) excluding the posterior pin guide (FIG. 7A), the center points of the posterior reference position determination holes 500 and the center points of the posterior rotation position determination holes 540 corresponding thereto included in each of the posterior pin guides 5 may be arranged horizontally at different heights, that is, may be arranged horizontally in different lines.

Preferably, angle indication marks 55 that show the degree of inclination of virtual straight lines L2, which connect the center points of the posterior reference position determination holes 500 and the posterior rotation position determination holes 540 that correspond to each other, relative to a horizontal reference line CL may be inscribed around the posterior reference position determination holes 500 and the posterior rotation position determination holes 540 corresponding thereto at each of the posterior pin guides 5.

The angle indication marks 55, for example, may be combinations of a number and a symbol (angle symbol), as exemplified in the figures, and the horizontal distance d2 from the center point of the posterior reference position determination hole 500 to the center point of the posterior rotation position determination hole 540 corresponding thereto may be 35 mm~50 mm when considering the anatomical shape of the anterior part of a distal femur.

The configuration in which two position determination holes are formed at each of the first anterior guide 40 and the second anterior guide 44 of each of the anterior pin guides 4 and two position determination holes are formed at each of the first posterior guide 50 and the second posterior guide 54 of each of the posterior pin guides 5 was exemplified and described above, but the number of position determination holes that are formed at each of the anterior guides and the posterior guides is not limited to two.

Depending on cases, the configuration may be changed into the type in which one position determination hole is formed at each of the first anterior guide 40 and the second anterior guide 44 of each of the anterior pin guides 4 and one position determination hole is formed at each of the first posterior guide 50 and the second posterior guide 54 of each of the posterior pin guides 5, so it should be noted that this type may also be included in the present disclosure.

In this case, in one of the plurality of anterior pin guides 4, the center point of the anterior reference position determination hole 400 and the center point of the anterior rotation position determination hole 440 may be arranged horizontally at the same height, and, in the other one, the center point of the anterior reference position determination hole 400 and the center point of the corresponding anterior rotation position determination hole 440 may be arranged horizontally at different heights.

Similarly, in one of the plurality of posterior pin guides 5, the center point of the posterior reference position determination hole 500 and the center point of the posterior rotation position determination hole 540 may be arranged horizontally at the same height, and, in the other one, the center point of the posterior reference position determination hole 500 and the center point of the corresponding posterior rotation position determination hole 540 may be arranged horizontally at different heights.

Figure 8:
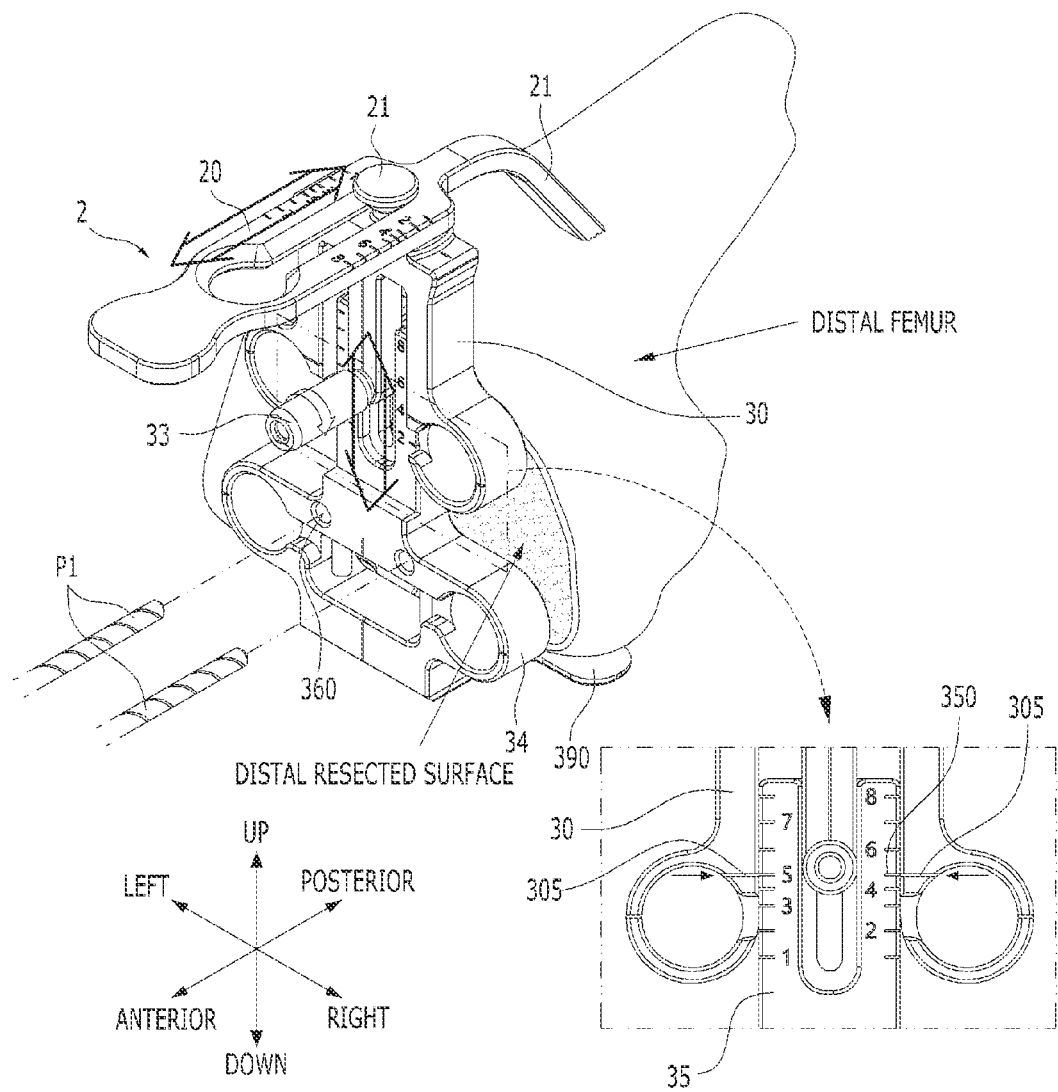
FIG. 8 is a use state view of the present disclosure showing measurement of the size of a distal femur that is performed using the femur size measuring device according to an embodiment of the present disclosure.

FIG. 8 is a use state view of the present disclosure showing measurement of the size of a distal femur that is performed using the femur size measuring device according to an embodiment of the present disclosure.

As shown in FIG. 8, in order to measure the size of a distal femur, a position is adjusted by moving forward and backward the stylus arm 20 in the figure with respect to the stylus holder 22 such that the stylus tip 21 comes in contact with a predetermined position on the anterior surface of the distal femur.

Further, in the state in which the lower AP sizer 34 can freely slide in the height direction with respect to the upper AP sizer 30 in the figure by releasing the locking member 33, the height of the lower AP sizer 34 relative to the upper AP sizer 30 is adjusted such that the pair of paddles 390 of the lower AP sizer 34 comes in contact with the surfaces of the condylus medialis and the condylus lateralis of the posterior part of the distal femur, respectively.

When the height adjustment is finished, a user maintains the height-adjusted state (the state in which the upper AP sizer and the lower AP sizer are restricted with respect to each other by the locking member) by turning the locking member 33 in the tightening direction, and then reads a size indication mark 350 on the surface of the connection member 35 that corresponds to the reference marker 305 of the upper AP sizer 30 or is positioned in a substantially same line as the reference marker 305, thereby selecting or determining the size of a femur component (component prosthesis).

If necessary, it may be possible to fix the femur size measuring device 1 according to an embodiment of the present disclosure on a distal resected surface of a femur by implanting fixing pins P1 into the pair of fixing pin insertion holes 360 formed at the body 36 of the lower AP sizer 34.

Figure 9:
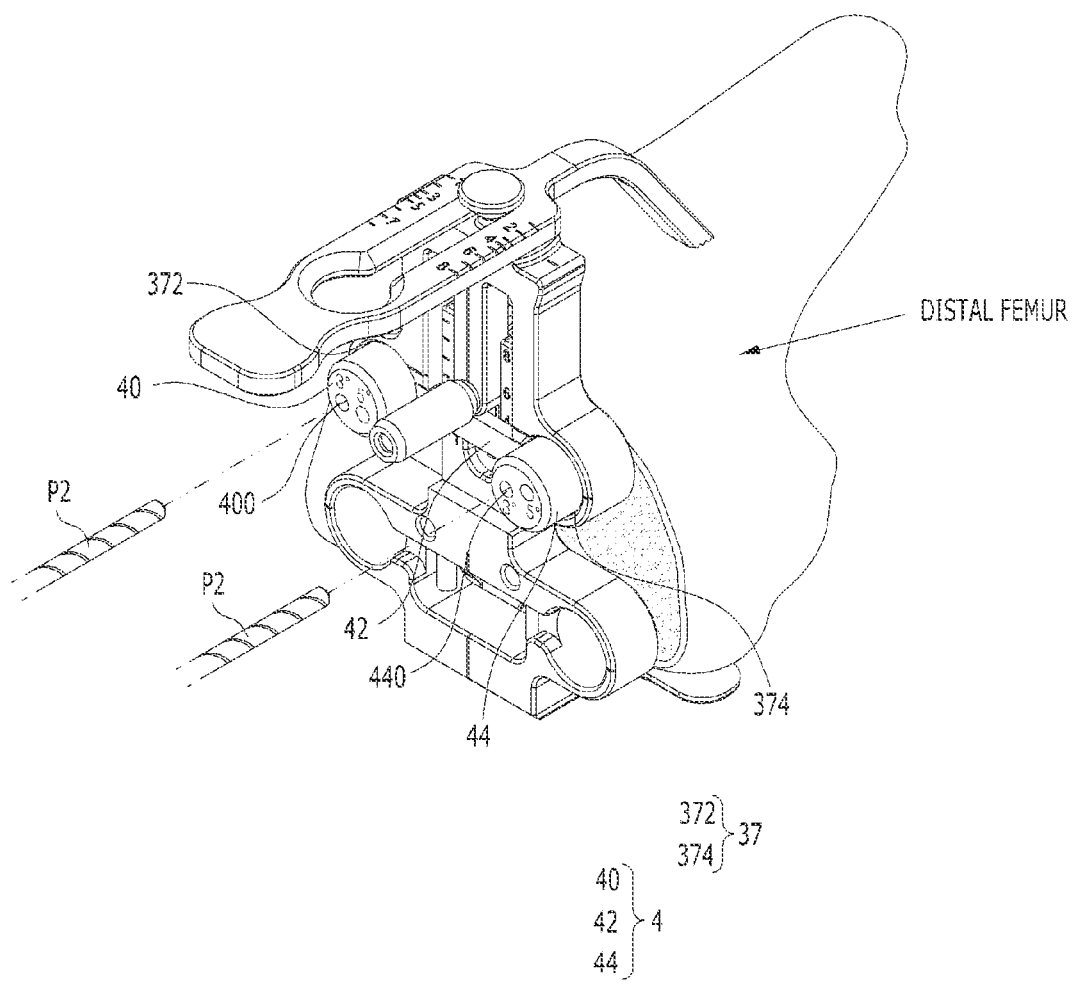
FIG. 9 is a view showing a process of implanting position determination pins, which determine a rotation position of a femur cutting guide to be attached to a distal resected surface, into a distal femur after measuring the size of a distal femur, that is, a view exemplifying a process of implanting position determination pins into the anterior part of a distal femur using an anterior pin guide.

FIG. 9 is a view showing a process of implanting position determination pins, which determine a rotation position of a femur cutting guide to be attached to a distal resected surface, into a distal femur after measuring the size of a distal femur, that is, a view exemplifying a process of implanting position determination pins into the anterior part of a distal femur using the anterior pin guide 4.

In order to implement the inherent natural knee joint motion of a patient, it is required to rotate a femur component a predetermined angel with respect to the transepicondylar axis (TEA) of a distal femur (not shown) and then implant the femur component in the distal femur in some cases. For example, it may be required to externally rotate the transverse center of a femur component by about 3° with respect to the TEA of a right femur when performing total knee replacement on a right leg.

In this case, a user checks the left and right directions of the anterior pin guide 4 and then, as shown in FIG. 9, mounts the anterior pin guide 4 into the anterior pin guide mount 37. In detail, a user mounts the anterior pin guide 4 into the anterior pin guide mount 37 such that the first anterior guide 40 of the anterior pin guide 4 is inserted into the first anterior pin guide mount hole 372 and the second anterior guide 44 is inserted into the second anterior pin guide mount hole 374.

Next, the user implants a pair of position determination pins P2 into a distal femur through a pair of position determination holes 400 and 440 fitting to 3° that is a desired angle. That is, as exemplified in FIG. 9, the user implants one position determination pin P2 into the distal femur through the anterior reference position determination hole 400 corresponding to 3° of the first anterior guide 40 and implants the other position determination pin P2 into the anterior part of the distal femur through the anterior rotation position determination hole 440 corresponding to 3° of the second anterior guide 44.

The rotation position of a femur cutting guide to be attached to a distal resected surface of the femur in the following process is determined by the pair of position determination pins P2 implanted in the distal femur through the anterior pin guide 4, and bone resection is performed on the distal femur in accordance with the determined rotation position of the femur cutting guide, whereby, as a result, a femur component can be attached in a rotated state by a predetermined angle, for example, externally 3° with respect to the distal femur.

Figure 10:
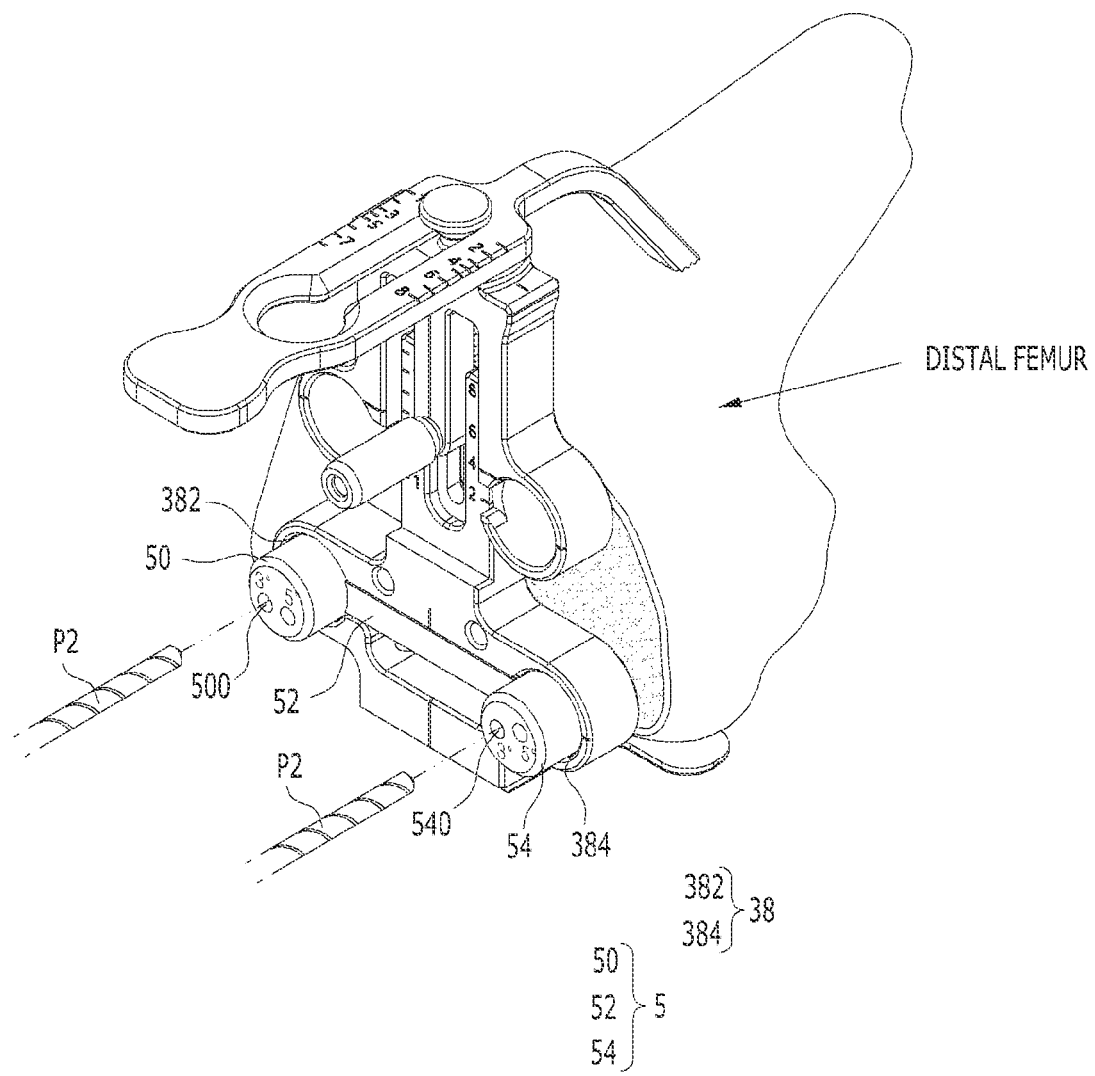
FIG. 10 is a view exemplifying a process of implanting position determination pins into the posterior part of a distal femur using a posterior pin guide.

FIG. 10 is a view exemplifying a process of implanting positioning pins into the posterior part of a distal femur using a posterior pin guide.

When a posterior pin guide is used to externally rotate the transverse center of a femur component by about 3° with respect to the TEA of a right femur in total knee replacement of a right leg, a user checks the left and right directions of the posterior pin guide 5 and then mounts the posterior pin guide 5 into the posterior pin guide mount 38, as in FIG. 10. In detail, a user mounts the posterior pin guide 5 into the posterior pin guide mount 38 such that the first posterior guide 50 of the posterior pin guide 5 is inserted into the first posterior pin guide mount hole 382 and the second posterior guide 54 is inserted into the second posterior pin guide mount hole 384.

Next, the user implants a pair of position determination pins P3 into a distal femur through a pair of position determination holes 500 and 540 fitting to 3° that is a desired angle. That is, as exemplified in FIG. 10, the user implants one position determination pin P3 into the distal femur through the posterior reference position determination hole 500 corresponding to 3° of the first posterior guide 50 and implants the other position determination pin P3 into the posterior part of the distal femur through the posterior rotation position determination hole 540 corresponding to 3° of the second posterior guide 54.

In this case, similarly, the rotation position of a femur cutting guide to be attached to a distal resected surface of the femur in the following process is determined by the pair of position determination pins P3 implanted in the distal femur through the posterior pin guide 5, and bone resection is performed on the distal femur in accordance with the determined rotation position of the femur cutting guide, whereby, as a result, a femur component can be attached in a rotated state by a predetermined angle, for example, externally 3° with respect to the distal femur.

According to the embodiment of the present disclosure described above, if necessary, it is possible to mount and use an anterior pine guide in an anterior pin guide mount (in the case of anterior referencing) or mount and use a posterior pin guide in a posterior pin guide mount (in the case of posterior referencing). That is, it is possible to perform appropriate surgical approach considering the shape of a femur of a patient or the difficulty of a corresponding surgical operation through one device even without using two kinds of femur size measuring device like in the related art.

Further, since pluralities of anterior pin guides and posterior pin guides are provided and pairs of position determination holes for determining the rotation position of a femur cutting guide are formed at different angles at the pin guides, it is possible to determine an appropriate implantation position or direction of a femur component (femur prosthesis) in the process of measuring the size of a distal femur when implementing the inherent natural knee joint motion of a patient.

Only a specific embodiment was described in the above detailed description. The present disclosure should not be construed as being limited to the specific embodiment described above, but should be construed as including all changes, equivalents, and substitutions within the spirit of the present disclosure defined in the claims.

What is claimed is:

1. A femur size measuring device that is a device used to measure the size of a distal femur to determine the size of a femur-side prosthesis (femur component) in total knee replacement, the femur size measuring device comprising:
   a stylus part including a stylus arm and a stylus holder to which the stylus arm is coupled to be able to move forward and backward;
   an anterior posterior (AP) sizer part having the stylus part coupled to an upper end thereof, having a pair of paddles at a lower portion thereof, and having an anterior pin guide mount and a posterior pin guide mount;
   a plurality of anterior pin guides mounted to be replaceable in the anterior pin guide mount, configured to determine insertion positions of a pair of anterior position determination pins for determining a rotation position of a femur cutting guide to be attached to a distal resected surface in a following process after a size of a distal femur is measured, and configured to guide the anterior position determination pins such that the anterior position determination pins can be accurately inserted at the determined insertion positions; and
   a plurality of posterior pin guides mounted to be replaceable in the posterior pin guide mount, configured to determine insertion positions of a pair of posterior position determination pins for determining a rotation position of a femur cutting guide to be attached to a distal resected surface in a following process after a size of a distal femur is measured, and configured to guide the posterior position determination pins such that the posterior position determination pins can be accurately inserted at the determined insertion positions.

2. The femur size measuring device of claim 1, wherein the AP sizer part includes:
   an upper AP sizer having the stylus part coupled thereto and having a seat with an open bottom;
   a lower AP sizer having the pair of paddles and a connection member that is coupled to the seat to be slidable up and down and has size indication marks inscribed on a surface thereof; and
   a locking member installed through portions of both of the upper AP sizer and the lower AP sizer to allow or restrict sliding of the connection member relative to the seat, and
   the anterior pin guide mount is formed at the upper AP sizer and the posterior pin guide mount is formed at the lower AP sizer.

3. The femur size measuring device of claim 2, wherein a fastening protrusion composed of an anterior fastening section and a posterior fastening section is formed in a predetermined height at a center of the seat,
   a fastening groove having an oblong hole is formed at the connection member in correspondence to the fastening protrusion, and
   a portion of the locking member is thread-fastened to a posterior through-hole of the posterior fastening section through both an anterior through-hole of the anterior fastening section and the oblong hole.

4. The femur size measuring device of claim 1, wherein the anterior pin guide mount has:
   a first anterior pin guide mount hole formed at a first side of the upper AP sizer constituting the AP sizer part; and
   a second anterior pin guide mount hole formed at a second side of the upper AP sizer to be symmetric to the first anterior pin guide mount hole.

5. The femur size measuring device of claim 1, wherein the posterior pin guide mount has:
   a first posterior pin guide mount hole formed at a first side of a body of the lower AP sizer constituting the AP sizer part; and
   a second posterior pin guide mount hole formed at a second side of the body to be symmetric to the first posterior pin guide mount hole.

6. The femur size measuring device of claim 5, wherein a paddle block is integrally formed under the body of the lower AP sizer, and the pair of paddles provided such that the condylus medialis and the condylus lateralis of a posterior part of a distal femur come in contact with the pair of paddles, respectively, when a size of the distal femur is measured is connected to the paddle block.

7. The femur size measuring device of claim 5, wherein a pair of fixing pin insertion holes in which fixing pins configured to fix the AP sizer part to a distal resected surface of a distal femur is formed at the body of the lower AP sizer.

8. The femur size measuring device of claim 1, wherein the anterior pin guides each include:
   a first anterior guide inserted in a first anterior pin guide mount hole or a second anterior pin guide mount hole of the anterior pin guide mount, and having an anterior reference position determination hole;
   a second anterior guide inserted in the second anterior pin guide mount hole or the first anterior pin guide mount hole, and having an anterior rotation position determination hole in correspondence to the anterior reference position determination hole; and
   a connection bridge connecting the first anterior guide and the second anterior guide to each other.

9. The femur size measuring device of claim 8, wherein one anterior reference position determination hole and one anterior rotation position determination hole are formed, respectively, at the first anterior guide and the second anterior guide of each of the anterior pin guides.

10. The femur size measuring device of claim 9, wherein a center point of the anterior reference position determination hole and a center point of the anterior rotation position determination hole of one of the plurality of anterior pin guides are arranged horizontally at the same height, and a center point of the anterior reference position determination hole and a center point of the corresponding anterior rotation position determination hole of the others are arranged at different heights.

11. The femur size measuring device of claim 9, wherein an angle indication mark showing the degree of inclination of a virtual straight line, which connects the center points of the anterior reference position determination hole and the anterior rotation position determination hole that correspond to each other, relative to a horizontal reference line is inscribed around the anterior reference position determination hole and the corresponding anterior rotation position determination hole.

12. The femur size measuring device of claim 8, wherein two anterior reference position determination holes and two anterior rotation position determination holes are formed, respectively, at the first anterior guide and the second anterior guide of each of the anterior pin guides.

13. The femur size measuring device of claim 12, wherein one of the plurality of anterior pin guides includes an anterior reference position determination hole and an anterior rotation position determination hole of which center points are arranged horizontally at the same height, and a center point of the anterior reference position determination hole and a center point of the corresponding anterior rotation position determination hole of the others are arranged horizontally at different heights.

14. The femur size measuring device of claim 8, wherein a horizontal distance from a center of the anterior reference position determination hole and a center point of the anterior rotation position determination hole is 25 mm~40 mm.

15. The femur size measuring device of claim 1, wherein the posterior pin guides each have:
   a first posterior guide inserted in a first posterior pin guide mount hole or a second posterior pin guide mount hole of the posterior pin guide mount, and having a posterior reference position determination hole;
   a second posterior guide inserted in the second posterior pin guide mount hole or the first posterior pin guide mount hole, and having a posterior rotation position determination hole in correspondence to the posterior reference position determination hole; and
   a connection bridge connecting the first posterior guide and the second posterior guide to each other.

16. The femur size measuring device of claim 15, wherein one posterior reference position determination hole and one posterior rotation position determination hole are formed, respectively, at the first posterior guide and the second posterior guide of each of the posterior pin guides.

17. The femur size measuring device of claim 16, wherein a center point of the posterior reference position determination hole and a center point of the posterior rotation position determination hole of one of the plurality of posterior pin guides are arranged horizontally at the same height, and a center point of the posterior reference position determination hole and a center point of the corresponding posterior rotation position determination hole of the others are arranged at different heights.

18. The femur size measuring device of claim 16, wherein an angle indication mark showing the degree of inclination of a virtual straight line, which connects the center points of the posterior reference position determination hole and the posterior rotation position determination hole that correspond to each other, relative to a horizontal reference line is inscribed around the posterior reference position determination hole and the corresponding posterior rotation position determination hole.

19. The femur size measuring device of claim 15, wherein two posterior reference position determination holes and two posterior rotation position determination holes are formed, respectively, at the first posterior guide and the second posterior guide of each of the posterior pin guides.

20. The femur size measuring device of claim 19, wherein one of the plurality of posterior pin guides includes a posterior reference position determination hole and a posterior rotation position determination hole of which center points are arranged horizontally at the same height, and a center point of the posterior reference position determination hole and a center point of the corresponding posterior rotation position determination hole of the others are arranged horizontally at different heights.

* * * * *